(12) United States Patent
Karadayi (10) Patent No.: US 10,932,749 B2
(45) Date of Patent: Mar. 2, 2021

(54) ULTRASOUND SYSTEM FOR ENHANCED INSTRUMENT VISUALIZATION

(71) Applicant: FUJIFILM SonoSite, Inc., Bothell, WA (US)

(72) Inventor: Kerem Karadayi, Seattle, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 626 days.

(21) Appl. No.: 15/347,697

(22) Filed: Nov. 9, 2016

(65) Prior Publication Data

US 2018/0125448 A1    May 10, 2018

(51) Int. Cl.
  *A61B 8/08*    (2006.01)
  *A61B 8/14*    (2006.01)

(52) U.S. Cl.
  CPC .............. *A61B 8/0841* (2013.01); *A61B 8/14* (2013.01); *A61B 8/5246* (2013.01); *A61B 8/5223* (2013.01)

(58) Field of Classification Search
  CPC ....... A61B 8/0841; A61B 8/5246; A61B 8/14; A61B 8/5223
  See application file for complete search history.

(56) References Cited

U.S. PATENT DOCUMENTS

| | | | |
|---|---|---|---|
| 5,908,390 A | 6/1999 | Matsushima | |
| 5,967,985 A * | 10/1999 | Hayakawa | A61B 8/0833 600/440 |
| 9,401,047 B2 | 7/2016 | Bogoni et al. | |
| 2004/0193042 A1 | 9/2004 | Scampini et al. | |
| 2011/0144495 A1* | 6/2011 | Wilkening | A61B 8/0883 600/443 |
| 2011/0249878 A1* | 10/2011 | Pagoulatos | A61B 8/0841 382/131 |
| 2012/0209107 A1 | 8/2012 | Guo et al. | |
| 2012/0253181 A1 | 10/2012 | Okamura et al. | |
| 2014/0187942 A1* | 7/2014 | Wang | A61B 8/0841 600/439 |
| 2015/0094569 A1 | 4/2015 | Ohuchi et al. | |
| 2015/0173706 A1 | 6/2015 | Andrews et al. | |
| 2015/0342561 A1* | 12/2015 | Takeda | A61B 8/0841 600/424 |

(Continued)

FOREIGN PATENT DOCUMENTS

| CN | 105496515 A | 4/2016 |
|---|---|---|
| WO | 2015136534 A1 | 9/2015 |

OTHER PUBLICATIONS

International Searching Authority, International Search Report and Written Opinion, International Patent Application PCT/US2017/059123, dated Jan. 25, 2013; 15 pages.

(Continued)

*Primary Examiner* — Jonathan Cwern
(74) *Attorney, Agent, or Firm* — Womble Bond Dickinson (US) LLP (57) ABSTRACT

An ultrasound imaging system includes a processor programmed to generate an anatomy image and a number of needle frames at different transmit beam angles. The system analyzes the data in the needle frames and selects segments therein that are identified as likely representing an interventional instrument. Data from one or more needle frames are blended with the data for the anatomy image of the tissue to create a composite image of the tissue and the interventional instrument.

20 Claims, 7 Drawing Sheets

(56) References Cited

U.S. PATENT DOCUMENTS

2016/0070436 A1     3/2016   Thomas et al.
2016/0317118 A1    11/2016   Parthasarathy et al.

OTHER PUBLICATIONS

PCT International Preliminary Report on Patentability for PCT/US2017/059123, dated Jun. 20, 2019, 6 pages.
Supplementary European Search Report for EP17868877 dated May 25, 2020, 2 pages.
Extended European Search Report for Application No. 17868877.6 dated Jun. 3, 2020, 9 pages.
European Patent Office Search Report for Application No. 115347697 dated Jun. 3, 2020, 9 pages.

\* cited by examiner

ULTRASOUND SYSTEM FOR ENHANCED INSTRUMENT VISUALIZATION

TECHNICAL FIELD

The disclosed technology relates to ultrasound imaging systems and in particular to ultrasound imaging systems for imaging interventional instruments within a body.

BACKGROUND

Ultrasound imaging is becoming increasingly accepted as the standard of care to be used when guiding an interventional instrument to a desired location within a body. One common use for this procedure is during the application of anesthesia, whereby a physician or a medical technician views an ultrasound image to help guide a needle to a desired nerve or a region of interest. To enhance the ability of the physician to view the needle, many ultrasound systems incorporate so called "needle visualization" technologies that produce a composite image from an anatomy image of the tissue and an image of the needle.

One of the common problems associated with most needle visualization techniques is that the beam direction of the ultrasound system used to image the needle has to be preset by the user. In order to obtain the best image, the transmit beam direction should be nearly perpendicular to a needle or other interventional instrument. If the needle does not appear clearly in the composite image of the tissue, then the user is supposed to change the settings on the machine to vary the beam direction. This is often too cumbersome for an unassisted operator when the operator has one hand holding the ultrasound probe and another hand guiding the needle. Even if the operator has an assistant, it is often distracting to instruct the assistant to change the beam direction settings, which may need frequent adjustment depending on how the probe is held and how the instrument is advanced into the body. Therefore, many procedures are performed where the transmit beam direction for visualizing a needle or other interventional instrument is not set in the optimal direction.

DETAILED DESCRIPTION

As will be explained in further detail below, the disclosed technology relates to improvements in ultrasound imaging systems and in particular to an ultrasound imaging system that is configured to produce a combined image of tissue and an instrument that is inserted into the tissue. In the description below, the interventional instrument is described as being a needle used to deliver anesthesia or other drugs to a desired location. However, other devices such as biopsy needles, needles for suturing tissue, needles for withdrawing fluids (e.g. amniocentesis), robotic surgical instruments, catheters, guidewires or other invasive medical instruments can also be imaged.

In one embodiment, a processor in the ultrasound system is configured to cause a number of transmit beams to be created and delivered to a body in order to produce an anatomy image of the tissue under examination. In addition, the processor is configured to cause a number of transmit beams to be generated at different transmit beam angles in order to image an interventional instrument. To distinguish the anatomy image from the images of the interventional instrument, the frames of the interventional instrument can be referred to as "needle frames," even if the instrument is not a needle.

Each of the needle frames produced from the transmissions at the different transmit angles is analyzed to detect the presence of an interventional instrument. In one embodiment, a composite image is created using the anatomy image and echo data from one or more of the needle frames that are captured using the different transmit beam directions in order to show both the tissue and the position of the interventional instrument.

Figure 1:
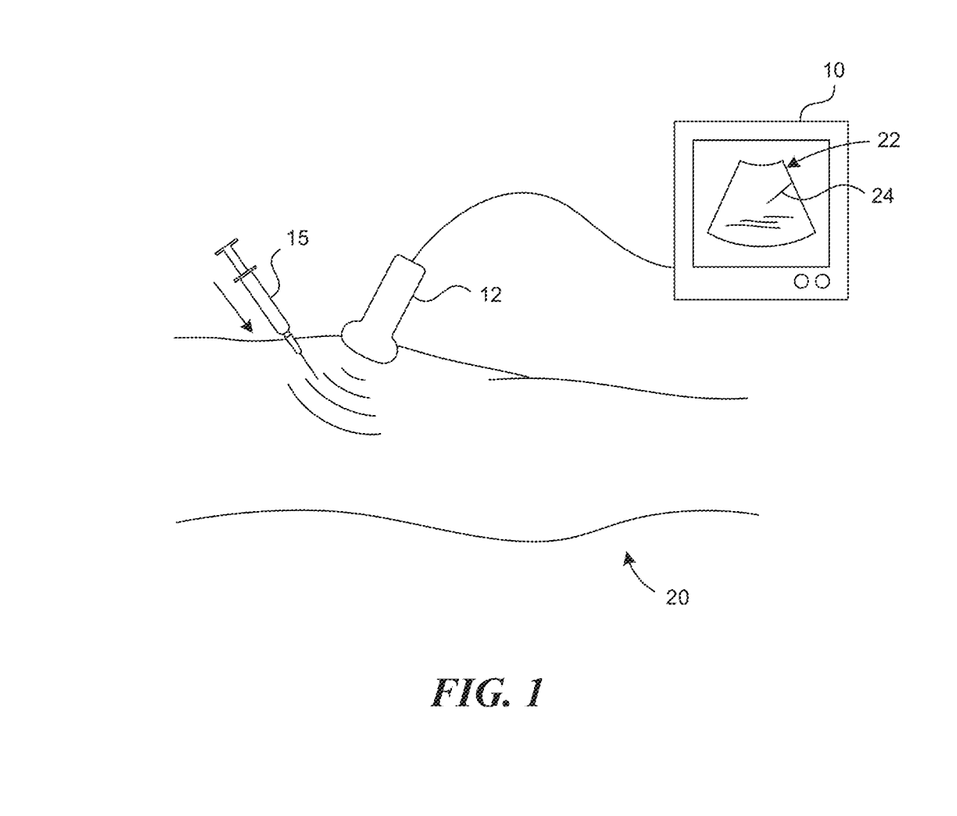
FIG. 1 is a simplified illustration of an ultrasound imaging system for producing and displaying a composite image of tissue and an interventional instrument in accordance with one embodiment of the disclosed technology.

FIG. 1 shows a representative ultrasound imaging system that implements the disclosed technology for imaging the tissue of a patient. In one embodiment, an ultrasound imaging system 10 can be a hand-held, portable or cart-based system that uses a transducer probe 12 to transmit ultrasound signals into a region of interest and to receive the corresponding echo signals in order to produce an image of the tissue being scanned. The probe 12 can be a one or two dimensional linear or curved transducer or a phased array transducer all of which can selectively change the transmit beam angles electronically.

The ultrasound imaging system 10 converts characteristics of the received echo signals (e.g. their amplitude, phase, power, frequency shift etc.) into data that is quantified and displayed for the user as an image. The images created may also be stored electronically for digital record keeping or transmitted via a wired or wireless communication link to another device or location. In some embodiments, an operator guides an interventional instrument 15 into the patient (or subject) 20 with one hand while holding the probe 12 with the other hand. The operator views a composite image 22 of the tissue and a representation 24 of where the interventional instrument is located in the tissue. The composite image 22 is updated on the screen while the instrument is guided to the target location. Such a location may be a particular nerve site in the field of anesthesia or other area of interest such as a vessel or a particular organ (e.g. uterus, prostate, tumor, heart vessel etc.).

As will be understood by those skilled in the art, the optimal beam direction for imaging a long thin interventional instrument is at an angle that is approximately perpendicular to the length of the instrument. However, the imaging parameters and beam directions required to image an instrument are often not the same as those that are optimal for imaging the tissue. In one embodiment of the disclosed technology, the user is not required to select a particular beam angle to use in generating the needle frames. Instead, the processor is programmed to generate needle frames using multiple different transmit beam angles. The echo data for the needle frames created from these different transmit beam angles are analyzed to detect the presence of objects that may be an interventional instrument. Echo data from one or more of the needle frames obtained using different transmit beam directions and that likely represent an interventional instrument are copied from the needle frames and blended with the echo data for the anatomy image in order to produce the composite image that shows both the tissue and the position of the interventional instrument.

Figure 2:
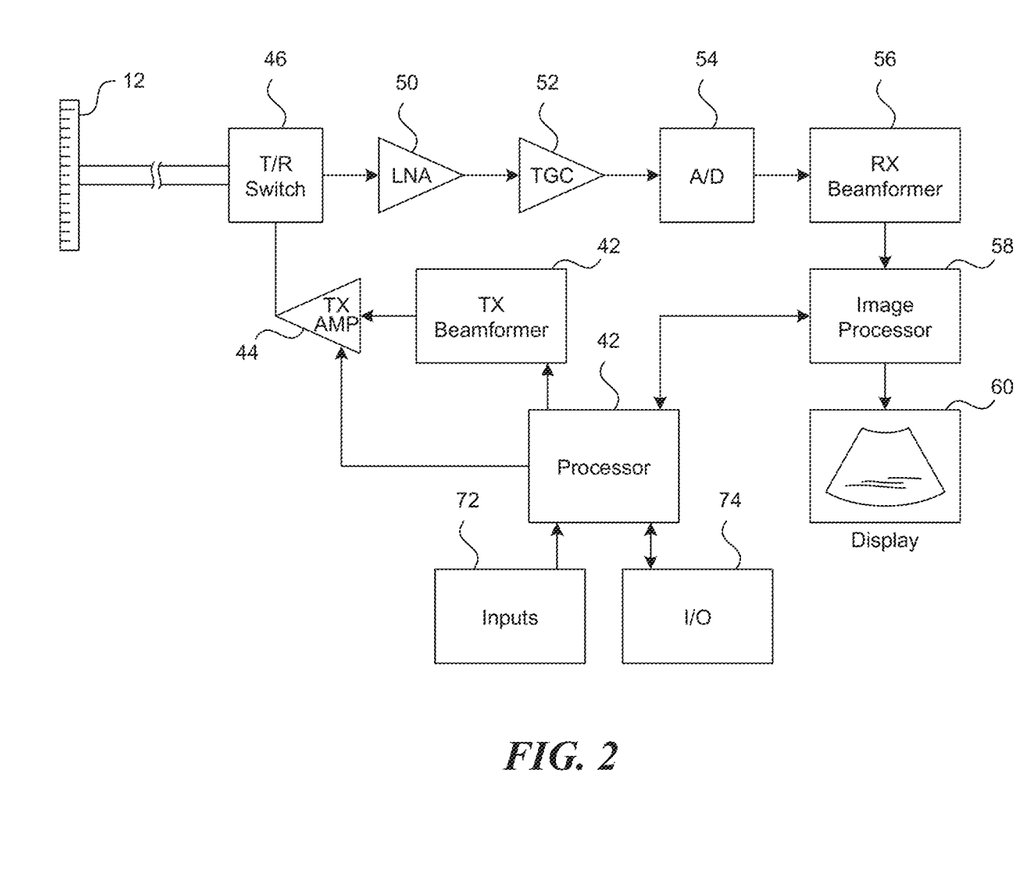
FIG. 2 is a block diagram of an ultrasound imaging system in accordance with an embodiment of the disclosed technology.

FIG. 2 shows a simplified block diagram of an ultrasound imaging system in accordance with an embodiment of the disclosed technology. As will be appreciated by those skilled in the art, the ultrasound system may be constructed with components that are different than those shown. In addition, the ultrasound system includes parts that are not discussed (e.g. a power supply etc.) and that are not necessary for the understanding of how to make and use the disclosed technology. In the embodiment shown, the ultrasound system includes a processor 40 having a built-in or external memory (not shown) containing instructions that are executable by the processor to operate the ultrasound imaging system as will be explained in detail below. In the transmit path, the ultrasound system includes a transmit beamformer 42, a transmit gain control amplifier 44 and a transmit/receive switch 46. If the ultrasound probe 12, is a phased array type or can otherwise change the angle of transmissions electronically, the transmit beamformer 42 operates to generate a number of signals having a relative amplitude and phase (timing) that are selected to produce an ultrasound beam from some or all of the transducer elements of the probe that constructively add in a desired transmit beam direction (the desired transmit beam angle). The signals from the transmit beamformer are amplified by the transmit amplifier 44 to a sufficiently high voltage level that will cause the transducer elements to produce the desired acoustic signals in the tissue being examined. In some embodiments, the processor 40 is connected to supply a control command such as a digital value (e.g. 0-255) to the gain control amplifier. The value of the command controls the amount of gain that is supplied by the transmit amplifier 44.

Other techniques for adjusting the power of the ultrasound signals include changing the waveforms that drive the transducer elements to either increase or decrease the power of the ultrasound signals. In another embodiment, the voltage rails (+V, −V) of an amplifier that produces the driving signals can be changed in order to vary the power of the ultrasound signals. In yet another embodiment, driving signals can be supplied to a lessor or a greater number of transducer elements to change the power of the ultrasound signals. Those skilled in art will understand that these techniques are merely exemplary and that there are numerous ways in which the level of acoustic power of the ultrasound signals delivered to the patient can be adjusted.

The amplified transmit signals are supplied to the transducer probe 12 through the transmit/receive switch 46, which disconnects or shields sensitive receive electronics from the transmit signals at the time they are delivered to the transducer probe 12. After the signals are transmitted, the transmit/receive switch 46 connects the receive electronics to the transducer elements to detect the corresponding electronic echo signals created when the returning acoustic waves impinge upon the transducer elements.

In the receive path, the ultrasound imaging system includes a low noise amplifier 50, a time gain control (TGC) amplifier 52, an analog to digital converter 54, a receive beamformer 56 and an image processor 58. Analog echo signals produced by the imaging probe are directed through the transmit/receive switch 46 to the low noise amplifier where they are amplified. The TGC amplifier 52 applies a variable amplification to the received signals that varies the level of amplification applied with the return time of the signals (e.g. proportional to the depth in the tissue being imaged) to counteract the attenuation of the signals versus depth. The amplified signals are then converted into a digital format by the analog to digital converter 54. The digitized echo signals are then delayed and summed by the receive beamformer 56 before being supplied to the image processor.

In some embodiments, the number of transmitted beams and received beams (lines) may differ from each other. For example, the receive beamformer may produce in parallel (i.e., simultaneously) two or more adjacent lines per transmitted beam, a technique sometimes known as parallel receive beamforming or multi-line processing. Multi-line processing may be used to increase the imaging frame rate by lowering the number of transmitted beams while still being able to keep the number of received lines per frame (line density) constant. Alternatively, a higher multi-line order (number of receive lines beamformed in parallel from a single transmitted beam) may be used to increase the number of received lines per frame while keeping the number of transmitted beams, hence the frame rate, constant. Other combinations of line density, frame rate and multi-line order are also possible. Furthermore, it is even possible to transmit an unfocused beam (plane wave) and beamform all the receive lines of a frame from that single transmitted beam. The system may also employ different combinations of line density and multi-line order for imaging the tissue vs. imaging an interventional instrument. However, it will be appreciated by those skilled in the art that use of a higher multi-line order, a lower-line density, or unfocused transmit beams, while improving the frame rate, may reduce the quality of the acquired images.

Images produced by the image processor 58 from the received signals are displayed on a display 60. In addition, the images can be recorded in an image memory (not shown) for future recall and review. A number of inputs 72 are provided to allow an operator to change various operating parameters of the ultrasound imaging system and to enter data such as the patient's name or other record keeping data. In addition, the ultrasound imaging system includes input/output (I/O) circuitry to allow the system to connect to computer communication links (LAN, WAN, Internet etc.) through a wired (e.g. Ethernet, USB, Thunderbolt, Firewire, or the like) or wireless (802.11, cellular, satellite, Bluetooth or the like) communication link.

The details of the components that comprise the ultrasound imaging system and how they operate are generally considered to be well known to those of ordinary skill in the art. Although the ultrasound imaging system is shown having many separate components, it will be appreciated that devices such as ASICs, FPGAs, digital signal processors (DSPs), CPUs or GPUs may be used to perform the function of multiple ones of these individual components.

As discussed above, the processor 40 is programmed to create a composite image of the tissue being examined and an interventional instrument being introduced into the tissue. In one embodiment, the image processor produces an anatomy image of the tissue being examined with imaging parameters that are selected for the depth and particular type of tissue being scanned. The anatomy image created by the image processor 58 is stored in memory to be combined with echo data for one or more of the needle frames that are created to locate an interventional instrument.

In one embodiment, the processor causes the transmit electronics to produce transmit beams in a number of different transmit directions to image the interventional instrument. For example, the processor 40 may direct transmit beams to be produced at a shallow, medium and steep angle as measured with respect to a longitudinal axis of the transducer probe. In most cases, the position of the instrument will show more clearly in one or more of the needle frames than in the others.

In one embodiment, the echo data for each of the needle frames created from the transmissions at the different transmit angles are analyzed for the presence of an interventional instrument. Various instrument detection algorithms can be used. For example, the images can be analyzed for the presence of a linear segment of pixels that are much brighter (e.g. greater amplitude) than adjacent pixels thereby indicating the presence of a strong linear reflector. The length of the segments that may represent an interventional instrument may vary and in some embodiments, may be curved if the interventional instrument itself is curved or bends when the instrument is inserted. Alternatively, the segments may seem to be curved in the coordinate system where detection is performed if the images were acquired using a curved transducer geometry (e.g., convex).

In one embodiment, each segment of bright pixels is scored to indicate how likely the segment represents an interventional instrument. Such a score can be adjusted by for example, the length of the bright pixels above a certain threshold, how straight or linear the segment of pixels is, how much contrast is present between the bright pixels and the adjacent pixels, how strong the edges around the segment of bright pixels are as determined by a gradient or other edge-detection operations, etc. A Hough transform or other similar techniques can be used to determine the location of pixels that lie on a linear or parameterized curved segment, from which a score can also be determined.

In one embodiment, the brightness data values for an image are converted into corresponding gradient values by looking at differences between adjacent brightness values along the beam lines. A needle or other bright reflector that is an interventional instrument is generally characterized by a large positive gradient (e.g. dark to light) in brightness values followed closely by a large negative gradient (e.g. light to dark) of brightness values when viewed in the direction from the transducer and into the tissue. The gradient values can be filtered to ensure that the large changes in the positive and negative gradient values occur within a distance that would be expected for the interventional instrument. Next, a Hough transform can be used to determine if the large positive/negative gradient changes occur in a linear pattern in the adjacent beam lines. Scores for the segments of large gradient changes can be increased or decreased depending on one or more of the length of the gradient changes, how close a positive gradient change is from a negative gradient change, how the gradient changes align spatially from beam to beam.

In one embodiment, segments of echo data are scored according to how large the gradients are and how well the gradients align in adjacent beam lines. Those segments having larger gradients and are more in line are given greater scores than those with smaller gradients and are less aligned. A representation of an instrument may comprise a single long segment or multiple shorter segments and not all segments having the highest score may originate from the same needle frame In one embodiment, echo data representing likely interventional instruments from those images with the highest scoring segments are copied from two or more needle frames and blended with the echo data for the anatomy image. In another embodiment, echo data are copied from a single needle frame and blended with the echo data for the anatomy image.

Other needle visualization techniques for detecting the presence of a needle or other interventional instrument in an ultrasound image could also be used.

In one embodiment, the processor is programmed to identify segments of pixel data from one or more of the needle frames created from the transmissions taken at the various transmit angles that have a score that indicates the pixels likely represent an interventional instrument. The processor copies the pixel data representing the instrument and uses a blending function to combine the copied pixel data with the pixel data in the anatomy image.

Figure 3A:
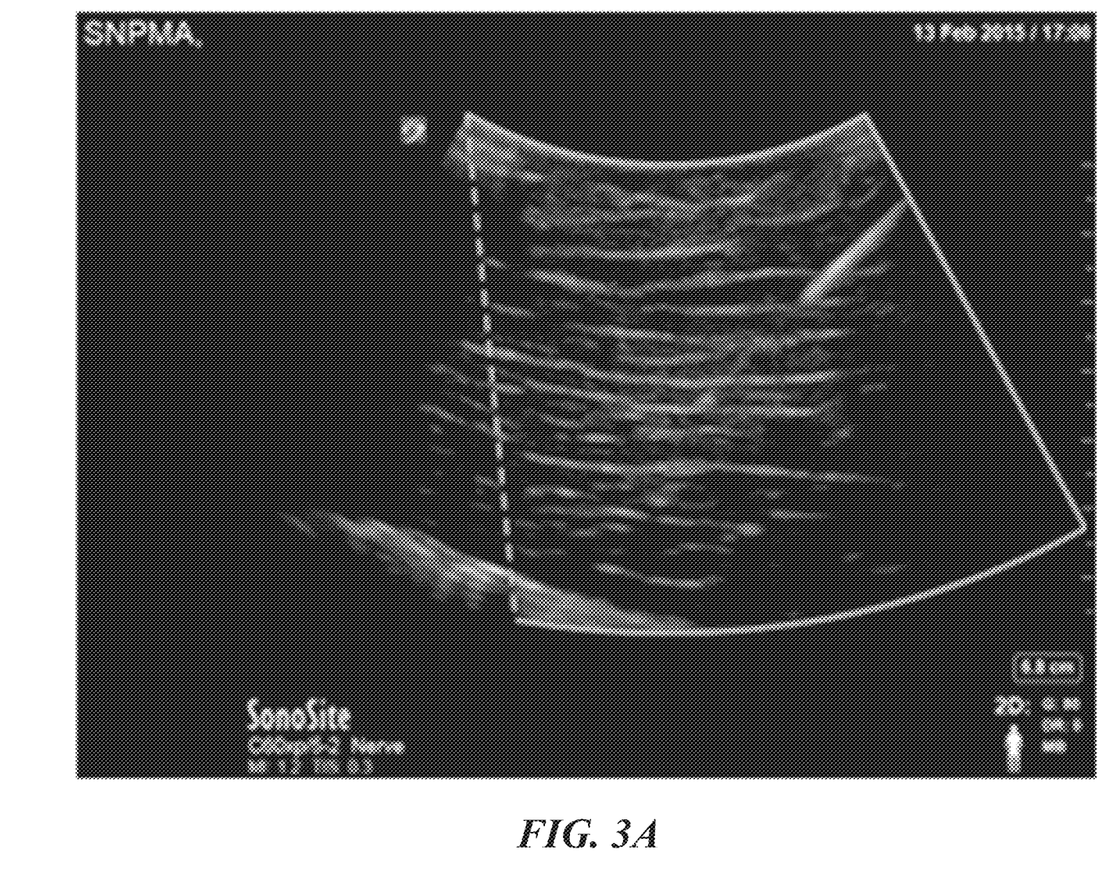
FIGS. 3A-3C show representative composite frames obtained by combining image data with echo data representing an interventional instrument from single needle frame transmissions at shallow, medium and steep transmit angles, respectively.
Figure 3B:
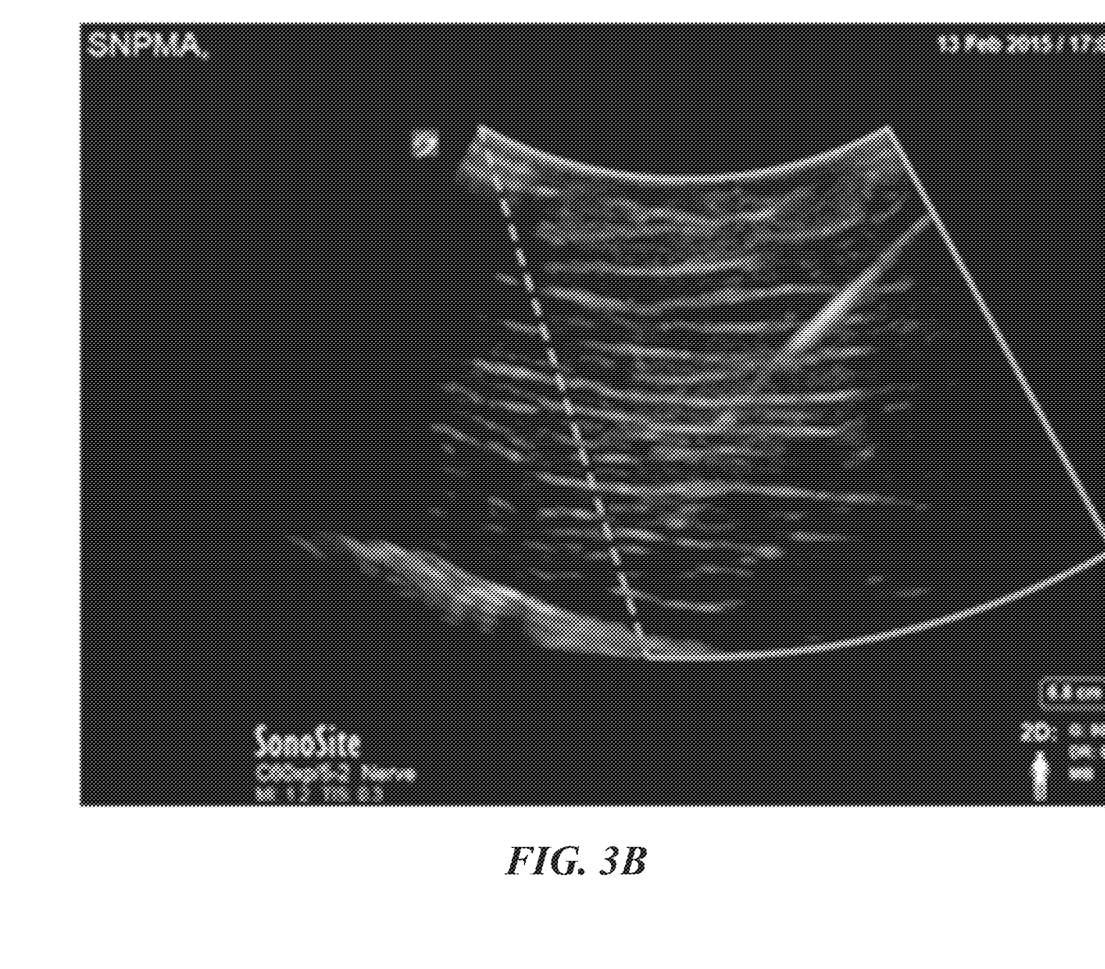
Figure 3C:
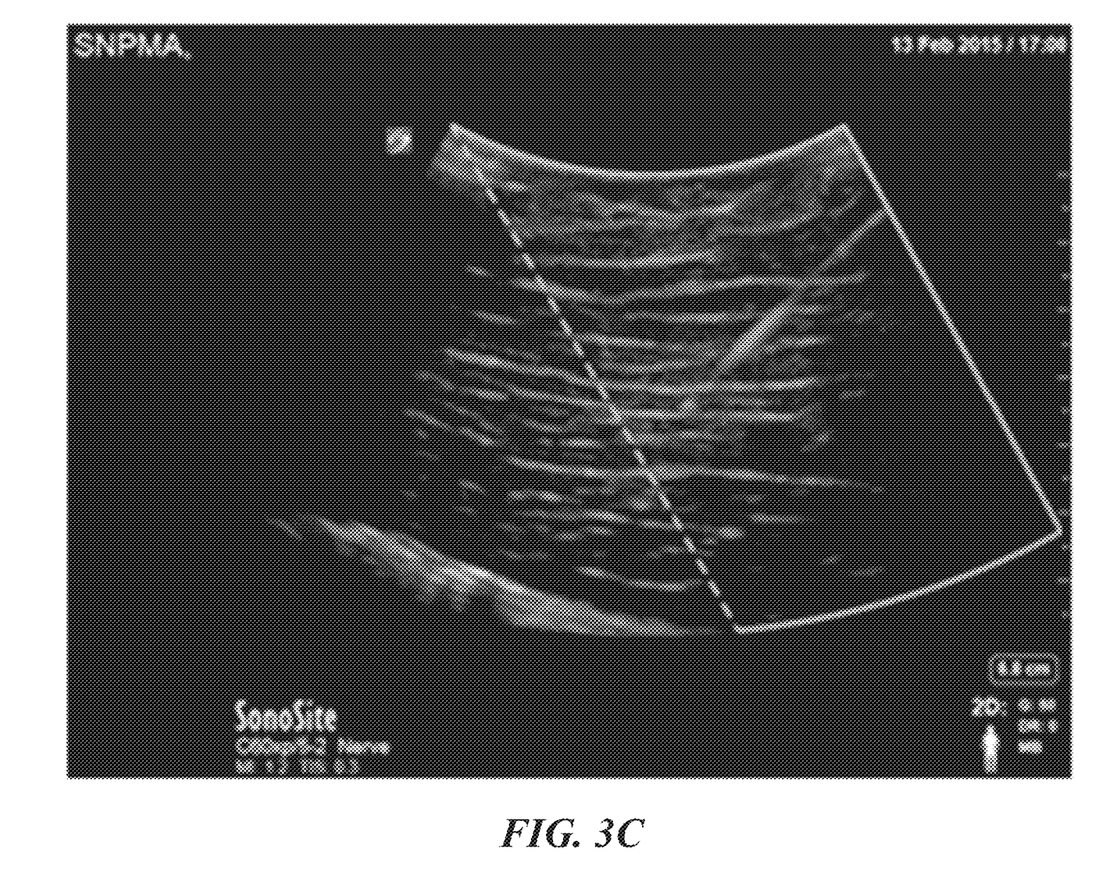

FIGS. 3A-3C show representative composite frames obtained by combining image data with echo data representing an interventional instrument from single needle frame transmissions at shallow, medium and steep transmit angles, respectively. In the composite frames shown, it can be seen that some needle frames show different parts of the interventional instrument better than others. In one embodiment, the processor copies the pixel data for various segments obtained using multiple firing angles that have the highest scores representing an interventional instrument and blends the copied segment pixel data into the anatomy image.

Figure 3D:
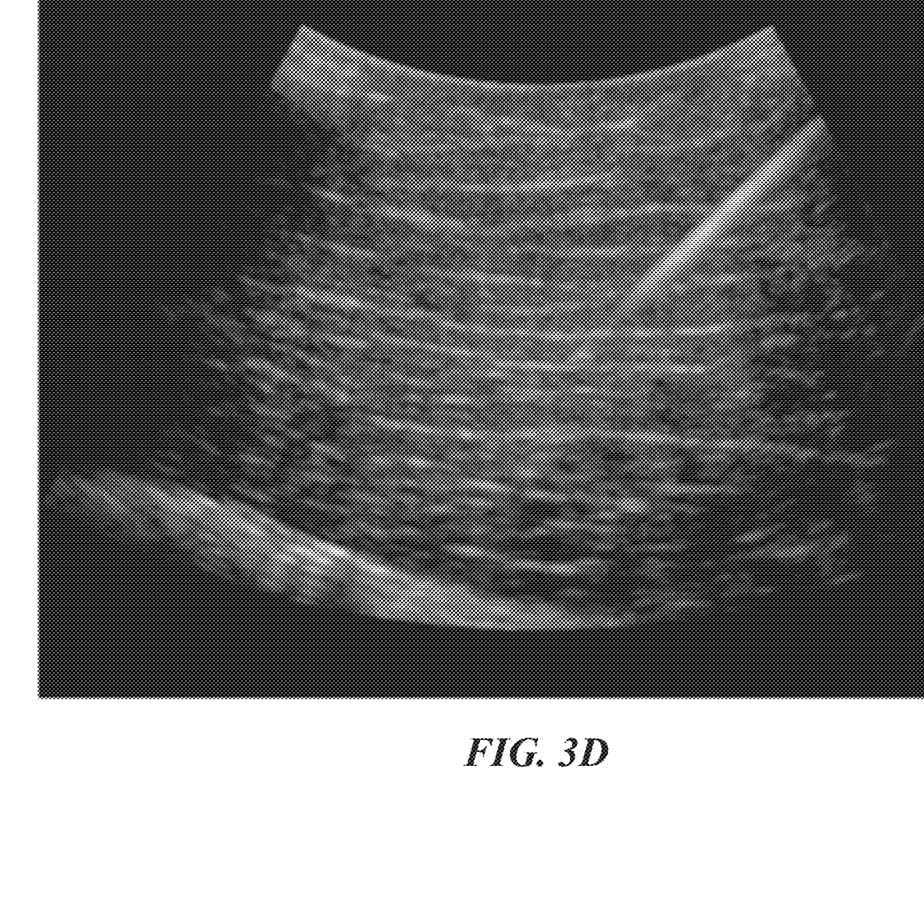
FIG. 3D illustrates a representative composite image created by blending echo data from one or more of the needle frames shown in FIGS. 3A-3C with echo data for an anatomy image in accordance with an embodiment of the disclosed technology.

FIG. 3D shows a representative composite image of the tissue that is created by blending pixel data copied from one or more of the needle frames obtained at different firing angles and that have a score indicating that the data likely represent an interventional instrument. In some embodiments, the data are blended with a feathering function so that the copied data representing the interventional instrument are seen strongly in the composite image while the copied data for areas surrounding the instrument blend in lightly with the data for the anatomy image so that the tissue surrounding the instrument can be seen.

Figure 4:
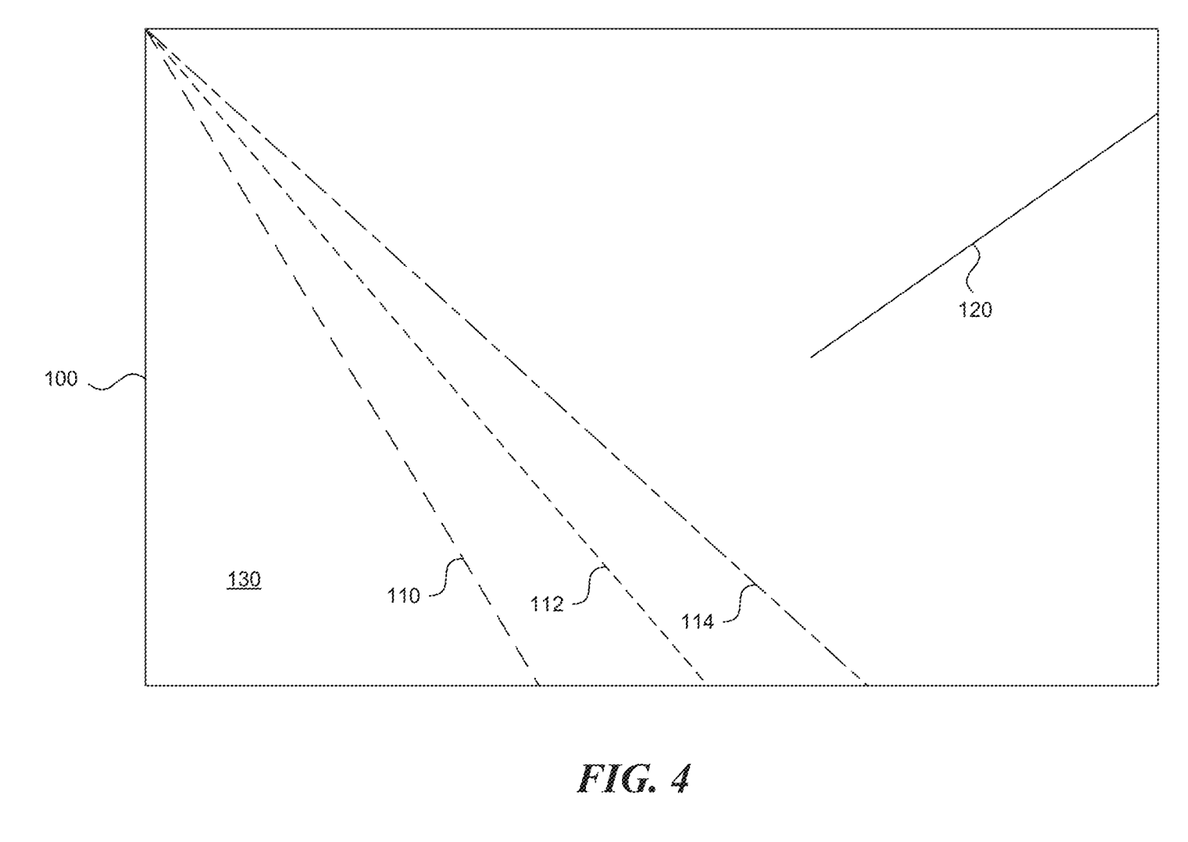
FIG. 4 shows a number of needle frames whereby one or more of the frame rate, line density or multi-line processing are adjusted for frames obtained with transmit beam angles that are not nearly perpendicular to the orientation of an interventional instrument in accordance with an embodiment of the disclosed technology.

FIG. 4 shows a representative region of interest into which a needle is inserted. In the example shown, an anatomy image 100 is obtained with a linear transducer. A number of needle frames are obtained at differing beam steering angles 110, 112 and 114. An interventional instrument 120 is inserted into the image. In the embodiment shown, the differences between the angle of insertion of the instrument and the angles that are perpendicular to the beam angles 110 and 112 are approximately equal. Therefore, the scores of the segments that represent the instrument in the needle frames created from firings in the beam steering angles 110 and 112 should be generally equal. Pixel data from each of these needle frames can therefore be copied and blended into the anatomy image 100. If the insertion angle of the instrument 120 were in a direction that was closer to a line perpendicular to the steering angle 114 for example, then pixel data from the needle frame that was created in response to the transmissions at the angle 114 would be copied and blended with the data for the anatomy image.

In the example shown in FIG. 4, the beam steering angles 110, 112 are determined to be the closest to being perpendicular to the insertion angle of the interventional instrument or are otherwise identified as producing the best image of the instrument based on the scores of the segments from the echo data received from these transmit angles. In one embodiment, the frame rate of transmissions at one or more of the angles 110 and 112 can be increased because they represent high priority angles, whereas the frame rate, line density or multi-line processing for the needle frame created from the beam steering direction 114 can be adjusted because that transmit angle is not a high priority angle as is explained further below.

In some embodiments, the pixel data used to display the ultrasound images are analyzed to detect the presence of an interventional instrument. However, it will be appreciated that the echo data that is not yet converted into pixel data that is ready for display could be analyzed. For example, echo data that has been amplified, converted to digital and beam-formed but not yet scan converted could be analyzed to detect and score segments in the data that represent interventional instruments.

As will be appreciated by those skilled in the art, creating a number of needle frames at different transmit angles can decrease the frame rate of the ultrasound imaging system. In one embodiment, the processor selects a higher line density and/or a lower multi-line setting for a subset of the needle frames (e.g. high-quality needle frames) than the rest of the needle frames (lower-quality needle frames), where the high-quality needle frame(s) is/are chosen adaptively based on the orientations of structures detected by the instrument detection algorithm with a high score (i.e. a high probability for the presence of an interventional instrument). If the detection algorithm finds structures of a similar orientation with high scores in multiple needle frames, the needle frame with an imaging steering angle that would insonate an interventional instrument at a close-to-perpendicular angle to the orientation of the probe can be chosen to be a high quality needle frame acquisition and the other needle frames can continue to be acquired as lower quality needle frames. This adaptively picked high-quality needle frame ensures a high quality visualization of the "most-probable" interventional instrument while the remaining lower-quality needle frames would ensure that instruments at other orientations are not missed and that an operator is not required to manually select a high-quality needle frame if the angle of the interventional instrument with respect to the ultrasound scan head changes during the procedure.

The system may also alter the number and acquisition rate of the needle frames and the angles employed adaptively based on the detection scores. For example, if features with high detection scores are identified within a needle frame with a certain angle setting, the system may designate that angle as a "high priority angle" and increase the acquisition rate of needle frames at or close to that angle setting, while dropping the acquisition rate of needle frames at angles farther away from the high-priority angle or for needle frames that do not contain features with high segment scores. In one embodiment, the system continues to acquire and analyze needle frames that have angles farther away from the high-priority angle setting as "scouting" needle frames so that the system can re-assess and change the "high-priority angle" on the fly if features with higher detection scores are detected with those scouting needle frames at any time. However, the angles of the scouting needle frames may be selected to have a larger angle spread between them and/or a lower acquisition rate to minimize the overall impact to the frame rate.

The subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium also can be, or can be included in, one or more separate physical components or media (e.g., multiple CDs, disks, or other storage devices).

The term "processor" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

From the foregoing, it will be appreciated that specific embodiments of the invention have been described herein for purposes of illustration, but that various modifications may be made without deviating from the scope of the invention. Accordingly, the invention is not limited except as by the appended claims.

I claim:

1. An ultrasound imaging system comprising:
an image processor that is configured to:
  acquire tissue echo data for an anatomy image of tissue being examined from received ultrasound signals; and
  acquire needle echo data for needle frames associated with the anatomy image that are obtained with transmit beam angles including a first transmit beam angle and a second transmit beam angle with respect to a longitudinal axis of a transducer probe that receives the received ultrasound signals; and
a processor that is configured to:
  determine, based on the needle echo data, segments in the needle frames obtained with the first transmit beam angle and the second transmit beam angle;
  assign scores to the segments in the needle frames, a first score of the scores assigned to a segment indicating that the segment represents an interventional instrument;
  identify at least one segment of the segments that is assigned the first score;
  set the first transmit beam angle as a priority angle when the at least one segment that is assigned the first score is detected in the needle frames with the first transmit beam angle; and
  acquire the needle frames with the first transmit beam angle at a first frame rate that is set based on the priority angle determination and acquire the needle frames with the second transmit angle at a second frame rate that is different from the first frame rate.

2. The ultrasound imaging system of claim 1, wherein the processor is configured to determine that the angle of the transmit beam used to acquire the needle echo data for the identified at least one segment of the segments is nearly perpendicular to the orientation of the interventional instrument based on the first score.

3. The ultrasound imaging system of claim 1, wherein the processor is configured to increase the first frame rate.

4. The ultrasound imaging system of claim 1, wherein the processor is configured to decrease the second frame rate.

5. The ultrasound imaging system of claim 1, wherein the processor is configured to:
identify the second transmit beam angle of the transmit beam as the priority angle when the at least one segment that is assigned the first score is detected in the needle frame with the second transmit beam angle;
acquire the needle frames with the second transmit beam angle at the first frame rate and acquire the needle frames with the first transmit angle at the second frame rate.

6. The ultrasound imaging system of claim 1, wherein the processor is configured to: increase a line density of the needle frames obtained at the first transmit beam angle.

7. The ultrasound imaging system of claim 1, wherein the processor is configured to:
decrease a number of receive lines that are beamformed in parallel for each transmit beam to produce the needle frames obtained at the first transmit beam angle.

8. The ultrasound imaging system of claim 1, wherein the processor is configured to:
decrease the second frame rate of the needle frames obtained at the second transmit beam angle.

9. The ultrasound imaging system of claim 1, wherein the processor is configured to:
decrease a line density of the needle frames obtained at angles that are not the first transmit beam angle.

10. The ultrasound imaging system of claim 1, wherein the processor is configured to:
increase a number of receive lines that are beamformed in parallel for each transmit beam to produce needle frames that are not obtained at the first transmit beam angle.

11. The ultrasound imaging system of claim 1, wherein the processor is configured to blend the at least one segment of the segments that is assigned the first score with the tissue echo data to create a composite image comprising the anatomy image of the tissue and the interventional instrument.

12. An ultrasound imaging system comprising:
an image processor that is configured to
  produce an anatomy image of tissue being examined from received ultrasound signals; and produce needle frames associated with the anatomy image that are obtained with different transmit beam angles including a first transmit beam angle, and a second transmit beam angle with respect to a longitudinal axis of a transducer probe that receives the received ultrasound signals;
a processor that is configured to
  determine, based on needle echo data, segments in the needle frames created with at least the first transmit beam angle and the second transmit beam angle;
  assign scores to the segments in the needle frames, a first score of the scores assigned to a segment indicating that the segment represents an interventional instrument;
  identify at least one segment of the segments that is assigned the first score;
  set the first transmit beam angle as a priority angle when the at least one segment that is assigned the first score is detected in the needle frame, and acquire the needle frames with the first transmit beam angle at a first frame rate that is set based on the priority angle determination and acquire the needle frames with the second transmit angle at a second frame rate that is different from the first frame rate.

13. The ultrasound imaging system of claim 12, wherein the processor is configured to blend the needle echo data from the at least one segment of the segments that is assigned the first score with tissue echo data for the anatomy image of tissue being examined.

14. An ultrasound imaging system comprising: an image processor that is configured to
produce an anatomy image of tissue being examined from received ultrasound signals; and produce needle frames associated with the anatomy image that are obtained with different transmit beam angles including a first transmit beam angle and a second transmit beam angle with respect to a longitudinal axis of a transducer probe that receives the received ultrasound signals;

a processor that is configured to determine, based on needle echo data, segments in the needle frames created with at least the first transmit beam angle and the second transmit beam angle;

assign scores to the segments in the needle frames comprising pixels, a first score of the scores assigned to a segment indicating that the segment represents an interventional instrument;

identify at least one segment of the segments that is assigned the first score;

set the first transmit beam angle as a priority angle when the at least one segment that is assigned the first score is detected in the needle frames with the first transmit beam angle; and acquire the needle frames with the first transmit beam angle at a first frame rate that is set based on the priority angle determination and acquire the needle frames with the second transmit angle at a second frame rate that is different from the first frame rate.

15. The ultrasound system of claim 14, wherein the processor is configured to adjust a frame rate of additional needle frames obtained with transmissions that are not in the priority angle beam steering direction.

16. The ultrasound system of claim 14, wherein the processor is configured to adjust line density of additional needle frames obtained at transmission angles that are not in the priority angle beam steering direction.

17. The ultrasound system of claim 14, wherein the processor is configured to adjust a number of receive lines that are beamformed in parallel from transmission angles that are not in the priority angle beam steering direction.

18. The ultrasound imaging system of claim 14, wherein the processor is configured to blend the pixels from the at least one segment of the segments that is assigned the first score with the pixels of the anatomy image of tissue being examined.

19. An ultrasound imaging system comprising: an image processor that is configured to produce an anatomy image of tissue being examined from received ultrasound signals; and receive needle echo data for needle frames associated with the anatomy image that are obtained with different transmit beam angles including a first transmit beam angle and a second transmit beam angle with respect to a longitudinal axis of a transducer probe that receives the received ultrasound signals;

a processor that is configured to determine, based on the needle echo data, segments in the needle frames that are created in response to the transmissions in at least the first transmit beam angle and the second transmit beam angle;

assign scores to the segments in the needle frames, a first score of the scores assigned to a segment indicating indicating that the segment represents an interventional instrument;

identify at least one segment of the segments that is assigned the first score set the first transmit beam angle as a priority angle when the at least one segment that is assigned the first score is detected in the needle frames with the first transmit beam angle; and acquire the needle frames with the first transmit beam angle at a first frame rate that is set based on the priority angle determination and acquire the needle frames with the second transmit angle at a second frame rate that is different from the first frame rate.

20. The ultrasound imaging system of claim 19, wherein the processor is configured to copy the needle echo data from the at least one segment of the segments that is assigned the first score to blend with tissue echo data for the anatomy image of tissue being examined.

* * * * *